(12) United States Patent
Conti

(10) Patent No.: US 8,795,214 B1
(45) Date of Patent: Aug. 5, 2014

(54) ORTHOTIC BRACE AND METHOD OF USING

(76) Inventor: Tony Conti, Prospect, KY (US)

( * ) Notice: Subject to any disclaimer, the term of this patent is extended or adjusted under 35 U.S.C. 154(b) by 597 days.

(21) Appl. No.: 12/838,987

(22) Filed: Jul. 19, 2010

(51) Int. Cl.
*A61F 5/00* (2006.01)

(52) U.S. Cl.
USPC .................................... 602/19; 602/5

(58) Field of Classification Search
USPC .............. 602/19, 5, 23; 2/311–313; 128/96.1, 128/100.1, 101.1, 876, 99.1; D24/190–192
See application file for complete search history.

(56) References Cited

U.S. PATENT DOCUMENTS

| | | | |
|---|---|---|---|
| 6,213,968 B1 | 4/2001 | Heinz et al. | |
| 6,322,529 B1 | 11/2001 | Chung | |
| 7,001,348 B2 | 2/2006 | Garth et al. | |
| 7,727,172 B2 * | 6/2010 | Wang | 602/19 |
| 2005/0251074 A1 * | 11/2005 | Latham | 602/19 |
| 2009/0082707 A1 * | 3/2009 | Rumsey | 602/19 |
| 2009/0204042 A1 * | 8/2009 | Park | 602/19 |
| 2010/0168630 A1 * | 7/2010 | Cropper et al. | 602/19 |
| 2010/0217167 A1 * | 8/2010 | Ingimundarson et al. | 602/19 |
| 2010/0268141 A1 * | 10/2010 | Bannister | 602/19 |
| 2011/0077567 A1 * | 3/2011 | Bledsoe | 602/19 |
| 2011/0213284 A1 * | 9/2011 | Garth et al. | 602/19 |
| 2012/0022419 A1 * | 1/2012 | Ingimundarson et al. | 602/19 |

OTHER PUBLICATIONS

M.I.H. International Inc., No. 574 M_Spine LSO, Sales Brochure, pp. 1-7, L-0637, www.m-brace.com, M.I.H International Inc., Montreal Quebec, Canada.
M.I.H. International Inc., No. 584 Low Profile M_Spine, Sales Brochure, pp. 1-7, L-0631, www.m-brace.com, M.I.H International Inc., Montreal Quebec, Canada.

* cited by examiner

*Primary Examiner* — Kim M Lewis
(74) *Attorney, Agent, or Firm* — Middleton Reutlinger

(57) ABSTRACT

An orthotic brace comprises a flexible panel having a first panel portion, a second panel portion and a central portion connecting the first and second panel portions, the first panel portion and the second panel portion being of sufficient length to wrap around a torso of a user, a closure structure disposed near ends of the first and second panel portions to secure the panel about the torso, an upper cord system and a lower cord system connected to the panel, the upper and lower cord systems being independently adjustable for a more anatomically correct fit and providing a mechanical advantage, the upper cord system and the lower cord system each having a first pull and a second pull, movable along upper and lower edges of the first and second panel portions, respectively, the first pull disposed at one of the first panel portion and the second panel portion, the second pull disposed at the other of the first panel portion and the second panel portion, wherein right side and left sides of the upper and lower cord systems may be tightened independently to tighten or loosen upper and lower portions of the orthotic brace at the central portion.

17 Claims, 17 Drawing Sheets

ORTHOTIC BRACE AND METHOD OF USING

CROSS-REFERENCE TO RELATED DOCUMENTS

None.

TECHNICAL FIELD

This invention pertains to an orthotic brace. More specifically, the present invention pertains to an orthotic brace having upper and lower adjustment on at least two halves of the orthotic brace.

BACKGROUND

Orthotic braces are commonly utilized, among other things, to alleviate pain suffered from back injuries and promote healing of post-operative back surgery. The braces typically are utilized to stabilize the spine or torso portion of the body. These braces typically fit snuggly around a patient's torso or trunk and are effective if worn properly.

Many back braces are difficult to appropriately position and fasten. In order to provide the aforementioned support and immobilization, the brace must be adjustable in order to be worn properly. Many patients have trouble utilizing such a brace and making necessary adjustments in order to provide the desired immobilization. If a brace is not easily and accurately adjustable, proper spinal support may not be achieved.

It would be highly desirable to provide an orthotic brace which is adjustable to a degree which is currently unavailable, which utilizes a cover to inhibit catching of adjustable parts on the user's clothing or body, and which is easy for a user to adjust without the aid of a doctor or medical professional.

SUMMARY

An orthotic brace comprises a flexible panel having a first panel portion, a second panel portion and a central portion connecting the first and second panel portions, the first panel portion and the second panel portion being of sufficient length to wrap around a torso of a user, a closure structure disposed near ends of the first and second panel portions to secure the panel about the torso, an upper cord system and a lower cord system connected to the panel, the upper and lower cord systems being independently adjustable for a more anatomically correct fit and providing a mechanical advantage, the upper cord system and the lower cord system each having a first pull and a second pull, movable along upper and lower edges of the first and second panel portions, respectively, the first pull disposed at one of the first panel portion and the second panel portion, the second pull disposed at the other of the first panel portion and the second panel portion, wherein right side and left sides of the upper and lower cord systems may be tightened independently to tighten or loosen upper and lower portions of the orthotic brace at the central portion. The orthotic brace further comprising a slidable sleeve. The orthotic brace wherein the sleeve is disposed over a central portion of the orthotic brace. The orthotic brace wherein the upper and lower cord systems further comprise cord anchors which are movably connected to said flexible panel. The orthotic brace wherein the cord anchors being spaced apart. The orthotic brace wherein the cord anchors being movable within the sleeve. The orthotic brace wherein the first panel portion and the second panel portion each having a pocket disposed between the central portion and distal ends, wherein a lateral pad is disposed in each of the pockets. The orthotic brace wherein each of the cords is connected to a pull strap. The orthotic brace further comprising lateral pad disposed in each of said first panel portion and said second panel portion. The orthotic brace wherein the lateral pad being curved about first and second axes.

An orthotic brace comprises a panel having a central portion, a first side panel portion and a second side panel portion, said panel being of sufficient length to wrap around a user's torso, a cord system including opposed cord anchors disposed generally centrally on the panel, a first cord connected to the anchors for adjustment of a lower portion of the system and a second cord connected to the anchors for adjustment of an upper portion of the system, the first cord having a first upper pull and a second upper pull, the second cord having a first lower pull and a second lower pull, the cord system allowing for separate tensioning of first side, second side, upper and lower portions of the cord system to provide improved conformance to the user's torso, a sleeve removably disposed about the central portion of the brace. The orthotic brace wherein the anchors comprise a base and a cover. The orthotic brace wherein the anchors further comprise cleats disposed between the base and cover, the cleats increasing mechanical advantage of the cord system. The orthotic brace wherein the anchors are movable within the sleeve. The orthotic brace further comprising pockets disposed in the first and second panel portions and a pad disposed in each of the pockets.

An orthotic brace comprises a panel having a first portion and a second portion, the first portion and a second portion extending from a central portion, a closure mechanism disposed at at least one end of the first portion or the second portion, a cord system having movable first and second anchors disposed on the central portion of the panel, the cord system having an upper cord system and a lower cord system for upper and lower adjustment of each of the first and second anchors, a pad disposed on the central portion on a side of the central portion opposite the first and second anchors. The orthotic brace wherein the pad is generally flat. The orthotic brace wherein the pad has a lordotic curvature contoured to approximate the curvature of a user's lower back. The orthotic brace wherein the pad further comprises wings disposed at upper and lower ends of the pad. The orthotic brace wherein the cord system provides a mechanical advantage of between about 4:1 and about 8:1.

A method of using an orthotic brace comprises wrapping the brace having a central panel portion and opposed side panel portions about a user's torso, closing the brace with a closure mechanism, ensuring the central portion is properly positioned at a lower back of the user, pulling a first cord system to tighten one of an upper or lower portion of the central panel portion and at least one of a right or left side of the central panel portion, pulling a second cord system to tighten the other of the upper and lower portion of the central panel portion and at least one of the right or left side of the central panel portion. The method of using an orthotic brace further comprising pulling the lower cord system firstly to move anchors connected to the central panel portion. The method wherein pulling the lower cord system secondly to move anchors connected to the central panel portion. The method further comprising pulling first and second pulls of the upper cord system and the lower cord system to tighten both left and right sides of said panel portion.

BRIEF DESCRIPTION OF THE ILLUSTRATIONS

Embodiments of the invention are illustrated in the following illustrations.

DETAILED DESCRIPTION

Figure 1:
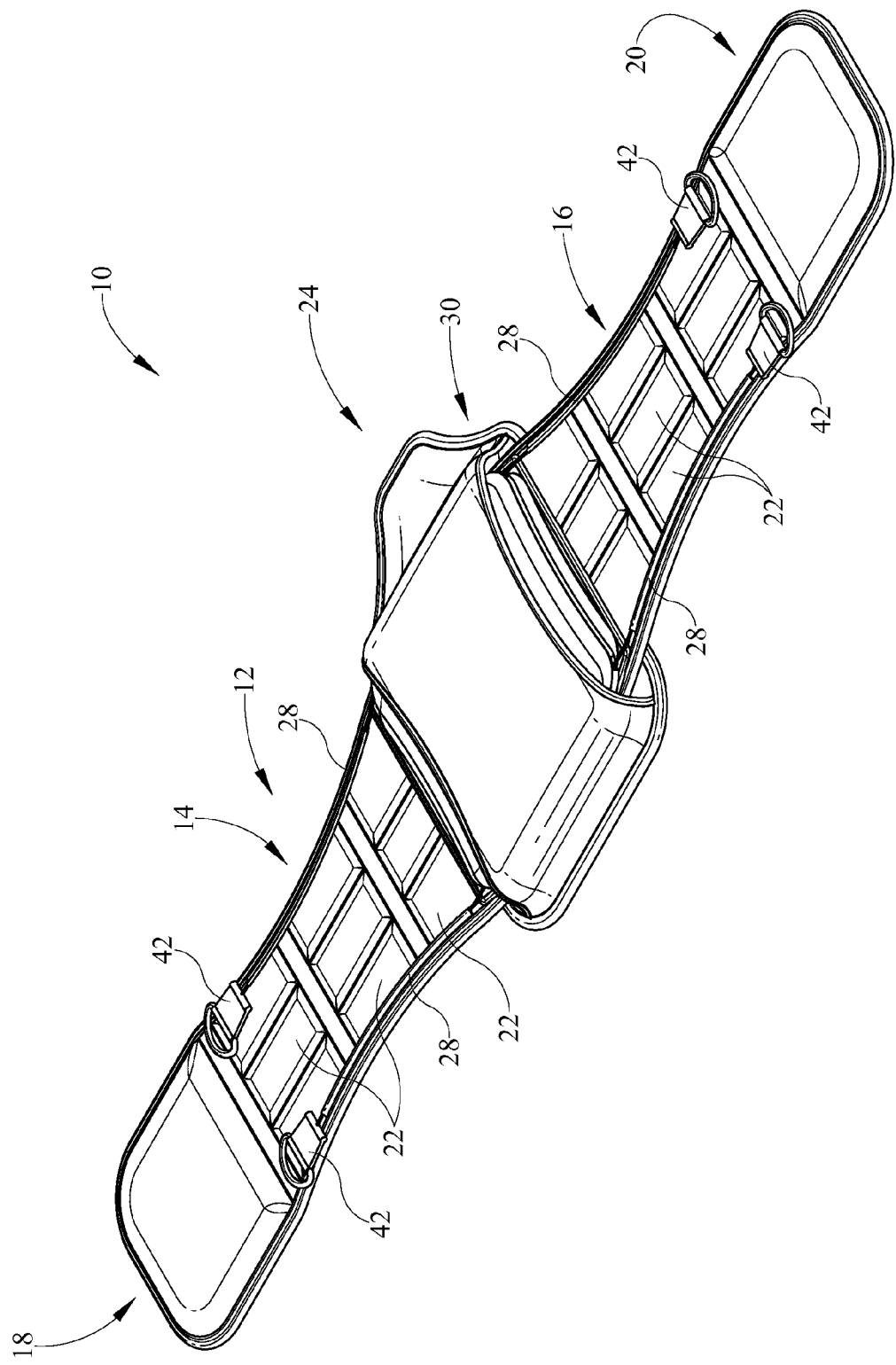
FIG. 1 depicts an upper rear perspective view of the orthotic brace.

It is to be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

Referring now to FIGS. 1-17, various embodiments of an orthotic brace is shown which utilizes a cord system to allow independent adjustment of the upper, lower, first side and second side portions of a cord system, and therefore increase lift and provide improved adjustability adjustment of the brace for a user. The brace is easily adjustable by a user without the need for a doctor or other medical professional while providing an accurate fit.

Referring initially to FIG. 1, a rear perspective view of the orthotic brace 10 is shown. The brace 10 is shown rear surface facing up, that is, the surface disposed away from the user or wearer. The front surface (not shown) is disposed against the wearer. The brace 10 utilizes a flexible panel 12 having a first portion 14, a second portion 16 and a central portion 24 which wrap around a user's torso to provide lower back support for the user. The panel 12 may be formed of neoprene, polyester or nylon covered neoprene or other such flexible but shape retaining material or materials. For example, as an alternative, the panel may be formed of VELCRO, moisture wicking, breathable, some combination thereof or other known materials. The first and second ends 18, 20 utilize closure structure or mechanisms 19, 21 to retain the brace 10 in a position about the user's torso. In the given example, the ends 18, 20 may utilize hook and loop material, commonly referred to as VELCRO, in order to retain the brace 10 about the user's torso. However, hook and loop should not be considered limiting as various alternative systems may be used, including for example, mechanical fasteners, buttons, latches, buckles, adjustable straps or various such closure mechanisms. The structures may be hook-in-loop mechanisms, buttons, clasps, locks with straps and/or buckles or any such structure which may retain the first end 18 and second end 20 together, so as to maintain the brace 10 about the user's torso.

The first portion 14 and the second portion 16 are joined distally from the first end 18 and second end 20 at a central portion 24. The first portion 14 and the second portion 16 may be integrally formed with the central portion 24 or may be joined in a separate manufacturing process, such as by glue, stitching, melt formed, or other known methods or some combination of known methods. The central portion 24 may be formed of the same material as the first and second portions 14, 16 or may be formed of a second material. The second material may also be less thick than the first and second portions 14, 16 to facilitate bending, folding or otherwise drawing of the material when a cord system 40 (FIG. 3) is tightened and released. The material of the central portion 24 folds with movement the cord system 40 and therefore allows for adjustment of the brace 10.

In the embodiment shown in FIG. 1, a sleeve 30 is slidably disposed over an end of the panel 12 and covers the central portion 24. The sleeve 30 covers the movable parts of the cord system 40, provides a location for indicia or such as private label information, and further as provides an aesthetically pleasing appearance. The sleeve 30 may further comprise or other known fastener material on a surface closest to the central portion 24 to aid in retaining the sleeve 30 in position. The sleeve 30 may further include a pad or other reinforcing element within the material defining the sleeve. The reinforcing element or stiffener of the instant embodiment may be flat according to the embodiment shown in FIG. 1, or may alternatively be curved as shown and described further herein at FIGS. 13 and 14.

The first and second panel portions 14, 16 may be embossed or padded with a plurality of ribs 22. These ribs 22 provide stiffening support for the panels 14, 16. As well, they may provide padding to add comfort for the user as well as providing an aesthetically pleasing appearance.

Figure 2:
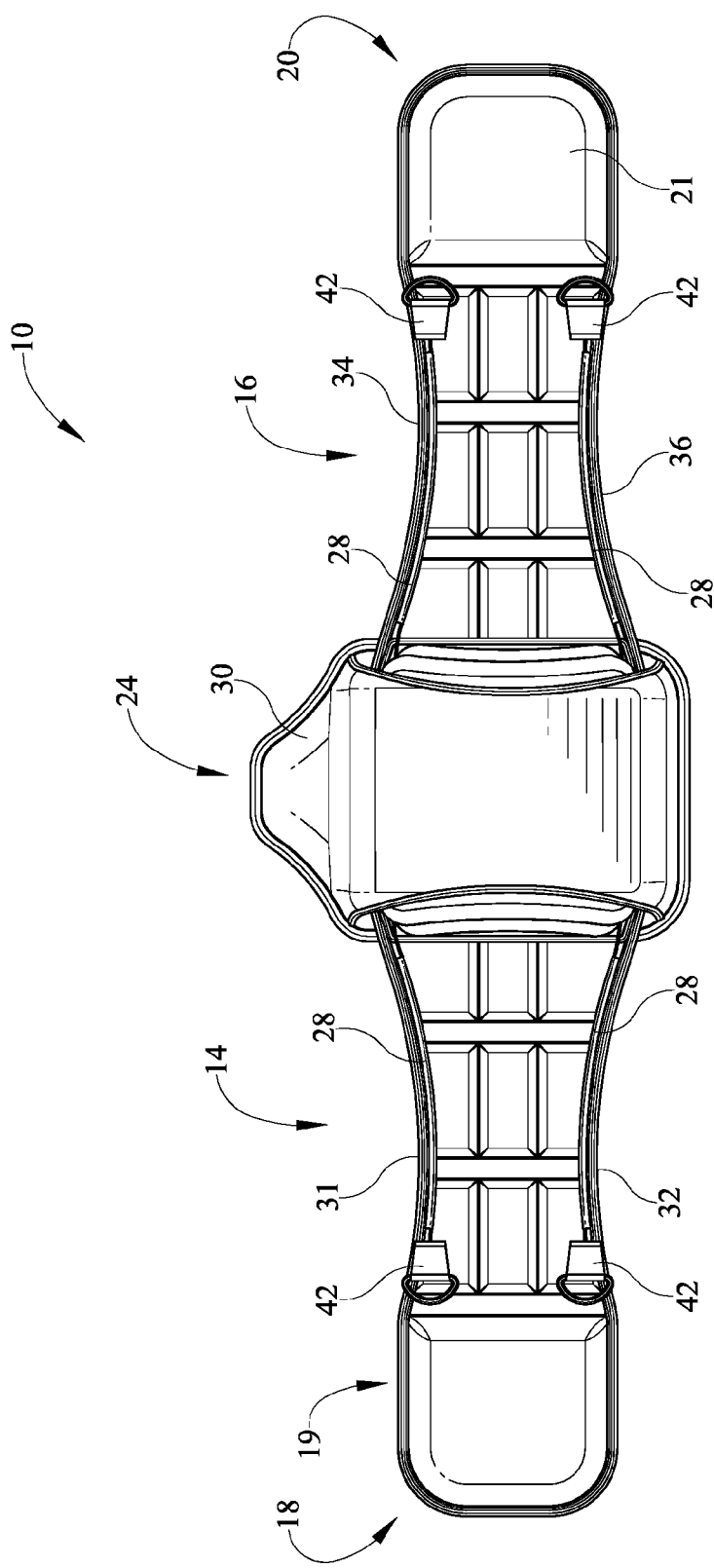
FIG. 2 depicts a rear view of the orthotic brace of FIG. 1.

Referring now to FIG. 2, a top view of the brace 10 is depicted again with the rear or outer surface facing up. The first panel portion 14 and the second panel portion 16 extend from the central portion 24, which is generally covered by the sleeve 30. The first panel portion 14 includes a first upper edge 31 on the left-hand side of the central portion 24 and a first lower edge 32 opposite the upper edge 31. The terms upper and lower edges are utilized with respect to the orientation of the brace as worn. The upper and lower edges 31, 32 extend from the central portion 24 to the first end 18 wherein the closure structure 19 is disposed. Similarly, the second panel portion 16 includes a second upper edge 34 and a second lower edge 36 extending from the right-hand side of the central portion 24. The second upper and lower edges 34, 36 extend from the central portion 24 towards the second end 20 wherein the closure structure is located.

Figure 3:
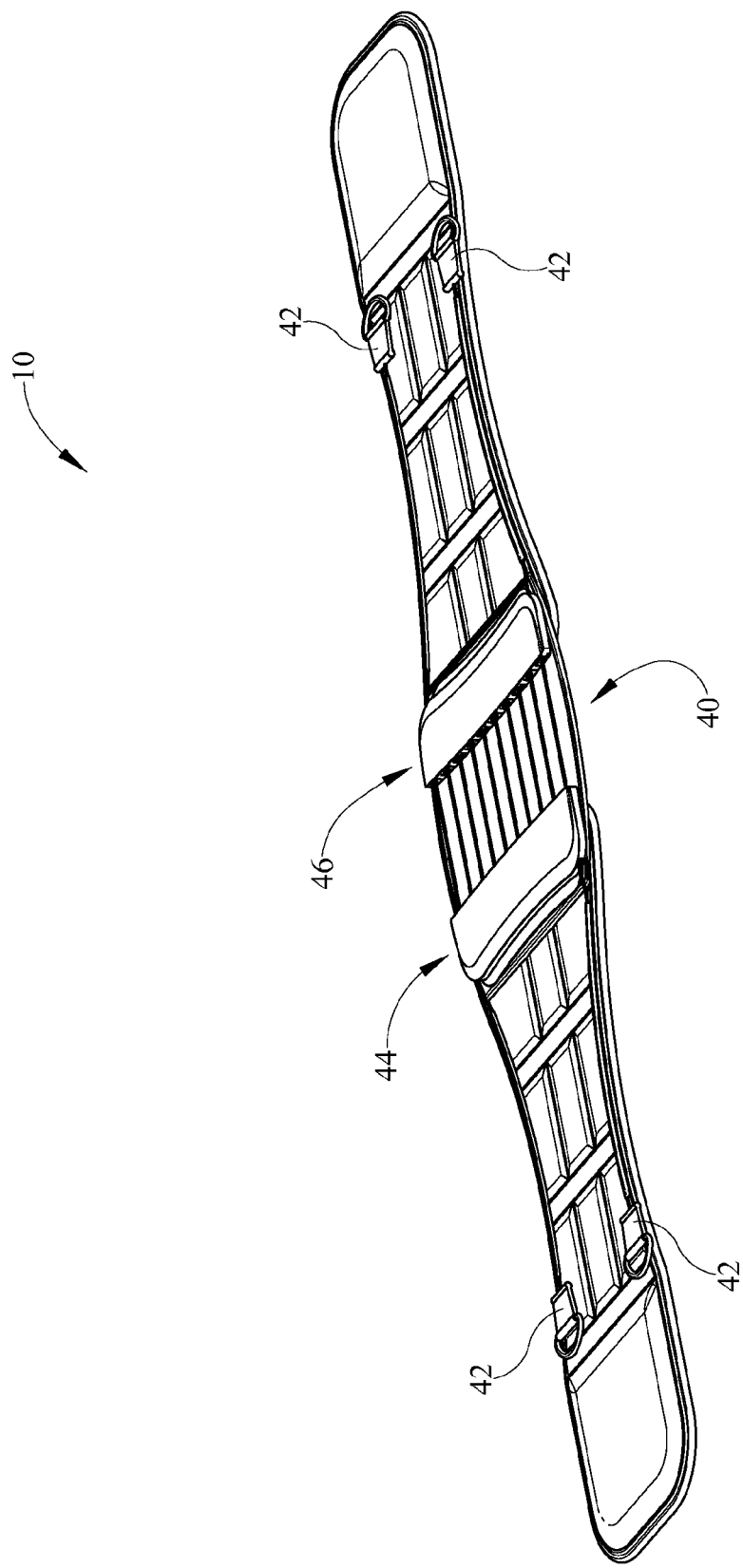
FIG. 3 depicts a upper rear perspective view of the brace with the sleeve removed.

Extending along the upper edges 31, 34 and the lower edges 32, 36 between the central portion 24 and the ends 18, 20 are cord or cable housings 28. The cord housings 28 may have various shapes and includes a hollow central portion through which cord 51, 53 (FIG. 4) pass. The cord housings 28 provide a conduit for passage of cords 51, 53 between the pulls 42 anchors 44,46 (FIG. 3). The cord housings 28 allow the cables to pass there through and move with the pulls 42 when the brace 10 is adjusted. The cord housings 28 also inhibit the cables from entangling in any of the adjacent components. The housings 28 also provide support for the cables when the cables are in a relaxed condition and thereby inhibit sagging.

The cords 51, 53 may be cords, cables, wires or other similar coupling structures. The cords may be formed of various materials including nylon, nylon based, cotton, wire, metallic or other material.

Figure 4:
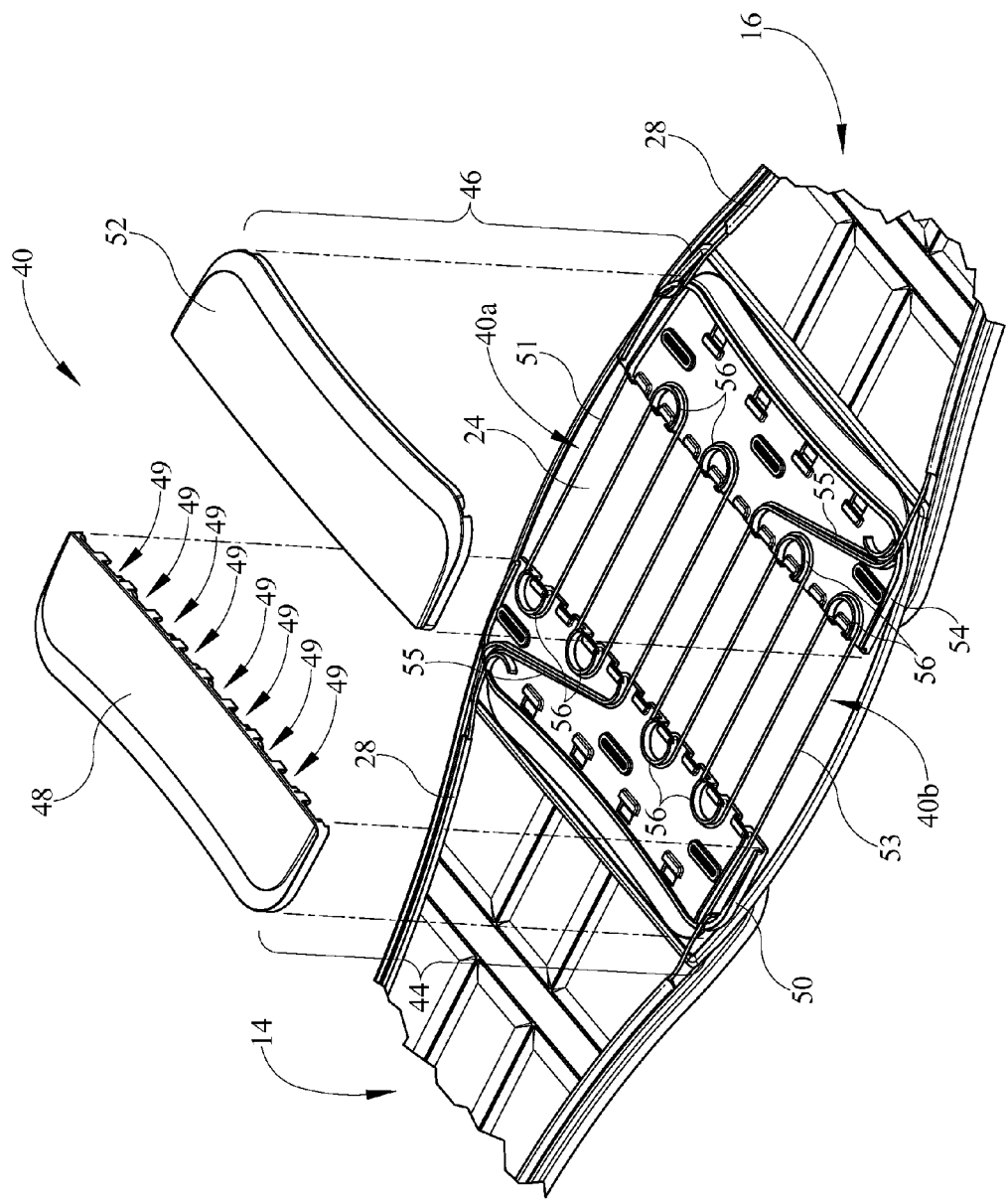
FIG. 4 depicts a perspective view of the cord system with covers exploded.

Referring now to FIG. 3, the orthotic brace 10 is shown, with the sleeve 30 removed, in perspective view. The orthotic brace utilizes a cord system 40 in order to allow adjustment of the brace. Additionally, the cord system 40 provides mechanical advantage in the range of from about 4:1 to about 8:1 which improves the ability of the user to adjust and tighten the brace 10. In the central portion 24 of the brace, the cords system 40 is depicted. The cord system 40 includes an upper cord system 40a and a lower cord system 40b (FIG. 4). In order to provide adjustment, the cord system 40 allows adjustment of anchors 44, 46. The anchors 44,46 are connected to the central panel 24 so as to cause tightening or loosening of the central panel 24. Specifically, the cord system 40 allows for left-hand and right-hand side adjustment, as well as upper and lower adjustments all within the area of the central portion 24. The pulls 42 are attached to the cords 51, 53 which extend through the cord housings 28 to the anchors 44, 46. The central portion 24 includes a first left-hand anchor 44 and a second right-hand anchor 46, each of which is movably independently adjustable with the pulls 42 at upper and lower ends. Again the terms upper and lower are used with respect to the orientation of the brace 10 in the worn position. When the pulls 42 are pulled by the user, the anchors 46 move toward one another, and the central portion 24 decreases in length as measured in the direction of the first end to the second end 18, 20. As the anchors move inwardly, the anchors 44, 46 place a force on the sides of the spinal area to lift, support and immobilize the spine. This relieves pressure on nerves in and around the spinal column, which are typically at the root of back pain. Additionally, this provides the bracing desired when the adjustment is proper. When the pulls 42 are released, the anchors 44, 46 spread apart, due to the force of the user's body, in the end-to-end direction.

Referring now to FIG. 4, a detailed view of the cord system 40 is depicted with the anchors 44 partially exploded. The cord system 40 includes the first and second anchors 44, 46 connected to the central portion 24 of the brace 10. Movement of the anchors causes tightening or loosening of the central portion 24 when the brace 10 is worn. The anchors 44, 46 each include a cover 48, 52 and a base portion 50, 54. The bases 50, 54 are connected to the central portion 24 so that when the bases 50, 54 move toward one another, the central portion 24 folds inwardly on itself allowing distance between the bases 50, 54 to decrease.

Figure 5:
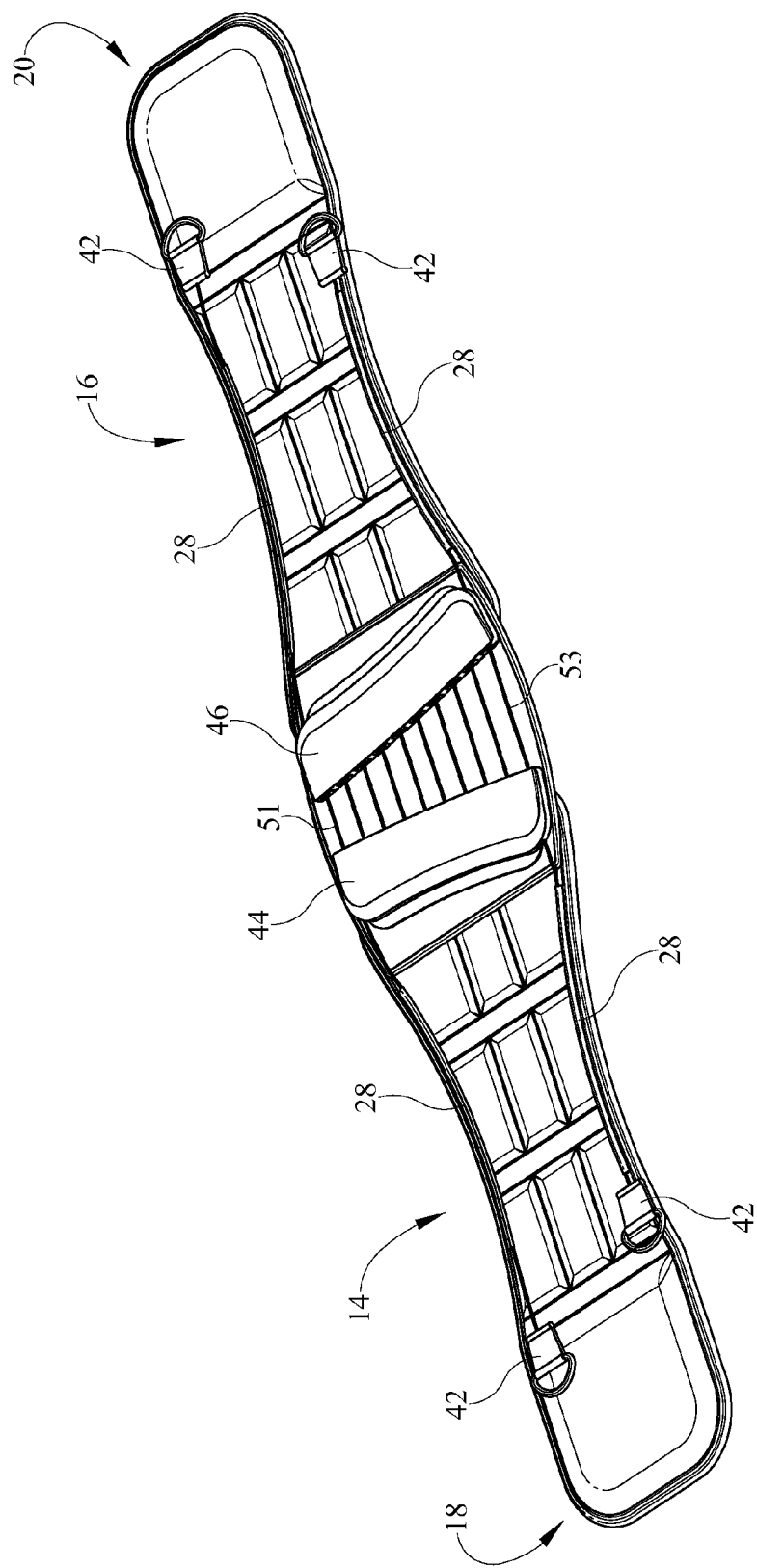
FIG. 5 depicts a perspective view of the brace with cord anchors in a first position.

Depicted within each of the bases 50, 54 are a plurality of semi-circular cleats 56. These cleats 56 are generally semi-circular in shape although various shapes may be utilized which utilized curvatures allowing movement of the cords 51, 53. The cord system cleats include an upper set and a lower set of cleats, considered as the brace 10 is oriented for use on a wearer, and corresponding to the upper cord system 40a and lower cord system 40b. FIG. 4 and FIG. 5, which depict the anchors 44, 46 removed, clearly show the sinuous cord paths of an upper cord 51 and a lower cord 53. The cleats 56 have walls extending from the lower surfaces of the bases 50,54 so that the cords 51, 53 may slide about the rounded cleat surfaces. As the cords 51, 53 pull against the cleats 56, the anchors 44,46 move toward one another to tighten the brace 10 at any or all of the upper or lower ends of the left or right hand anchors 44,46.

First, the upper cord system 40a includes the upper cord 51 that extends between the upper pulls 42 through cord housings 28 along, or adjacent to, the upper edges 31, 34 (FIG. 3) of the first and second panel portions 14, 16. As shown in FIG. 4, the cord entering the base portion 50 moves through a guide 55 which properly positions the cord 51 to serpentine through the upper cleats 56. The guide 55 directs the cord 51 from the housing 28 downward to begin the sinuous path about the plurality of cleats 56 on the first base 50 and the second base 54. The cord 51 exits the base 54 near the upper edge of the second panel portion 16 and moves through the cable housing 28 to the upper pull 42 located on the second panel portion 16.

Similarly, the lower cord system 40b includes the lower cord 53 that extends between the first panel portion 14 and the second panel portion 16 generally along the lower edges of those panel portions and between the first and second lower pulls 42. The cord 53 passes from the cable housing 28 of the second panel portion 16 through a lower guide 55 which positions the cord 53 more centrally with respect to the central portion 24. Such positioning allows the cord 53 to serpentine between the cleats 56 of the bases 50, 54. Additionally, the cord 53 exits through the lower portion of the anchor base 50 through the cable housing 28 and out to the pull 42 of the first panel portion 14. As clearly shown in FIG. 4, the cord guides 55 allow positioning of the cords 51, 53 more centrally between the cord system 40. Although the guides 55 are shown at the upper end of base 50 and lower end of base 54, the guides 55 could alternatively be placed at the lower portion of base 50 and upper portion of base 54. Additionally, the cleats 56 and the guides 55 could be located in the covers 48, 52 for operation.

As shown in FIG. 4, the covers 48, 52 are exploded from the bases 50, 54. The covers 48, 52 include opposed facing edges having a plurality of apertures or windows 49 through which the cords 51, 53 pass between the anchors 44, 46 as seen in FIGS. 3 and 4. The cords 51, 53 may then pass between the anchors 44, 46 in serpentine fashion to provide adjustability for the central portion 24 of the brace 10.

Referring now to FIG. 5, the brace 10 is depicted in perspective view with the central portion 24 cinched for tightening. Specifically, the upper pulls 42 are tightened so that the upper ends of the anchors 44,46 are pulled closer in proximity. In this view, the upper pulls 42 are spaced apart farther than the lower pulls 42 due to the tightening of the upper cord system 40a. The pulls may include a fastening structure such as a hook and loop material or the like to retain the pulls near ends 18, 20 when the cord 51 is tightened.

Figure 6:
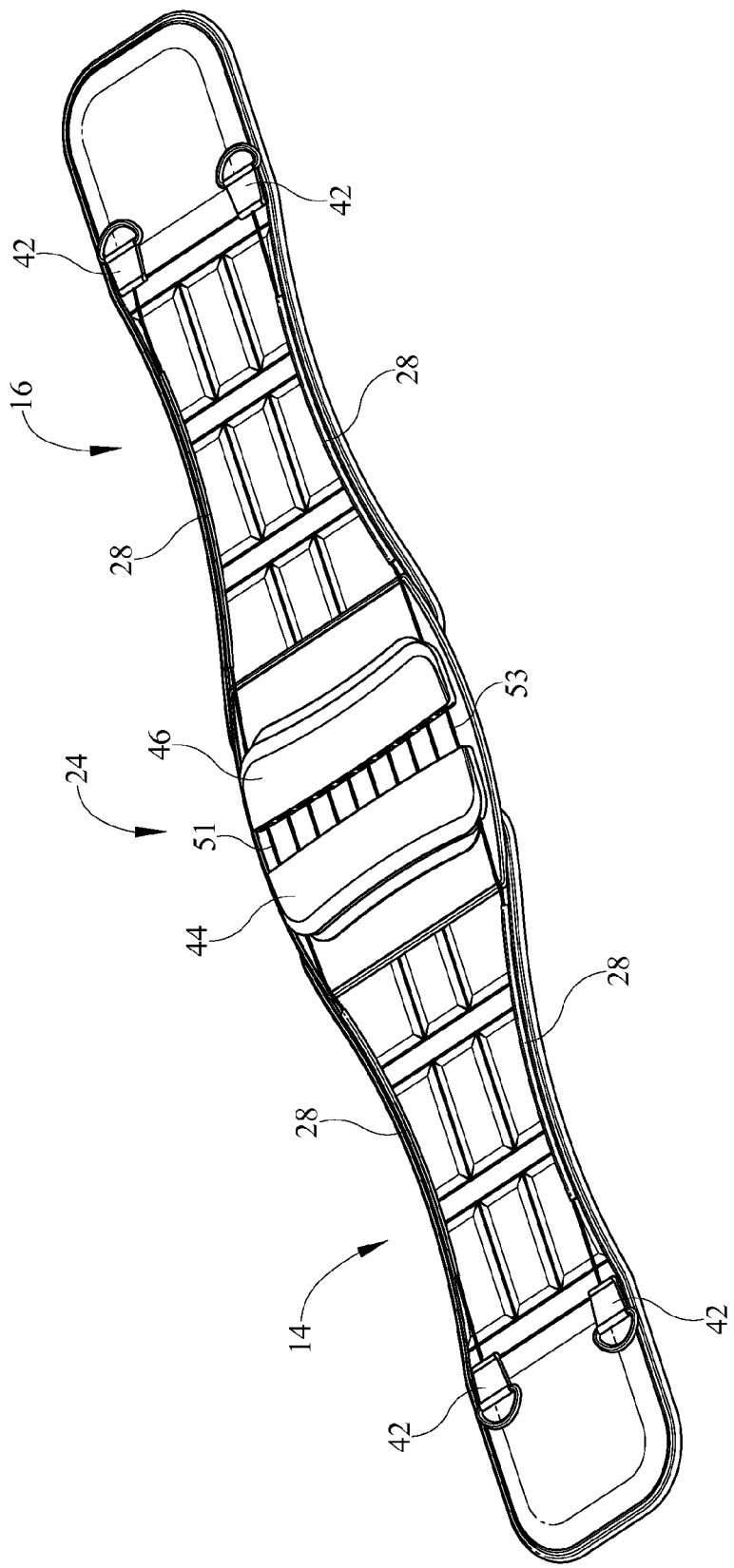
FIG. 6 depicts a perspective view of the brace with the cord anchors in a second position.

Referring now to FIG. 6, the brace 10 is depicted with the lower pulls 42 utilized to tighten the lower half of the central portion 24. Specifically, the upper pulls 42 of the first and second panel portions 15, 16 are tightened to cinch the upper half of the central portion 24, as previously described. Additionally, the lower pulls 42 of the first and second panel portions 14, 16 may be utilized to tighten the lower portions of the central panel 24. As depicted, the lower pulls 42 may be cinched to tighten the lower half of the central portion 24. When the upper and lower pulls 42 are utilized, the anchors 44,46 become aligned and in closer proximity at the top near the tops and bottoms. However, it will be understood by one skilled in the art that the anchors 44,46 are parallel due to the brace not being worn in the illustrated example. When the brace 10 is worn, the anchors 44, 46 may not be tightenable to the extent that the two anchors 44,46 are parallel. Thus depending on the body size and shape of the wearer, the upper ends of the anchors 44,46 may be closer together or the lower ends of the anchors may be closer together. In any event, the cord system 40 provides for independent left, right, upper and lower adjustments in the lumbar area to increase lift, immobilization and back support for the user.

Figure 7:
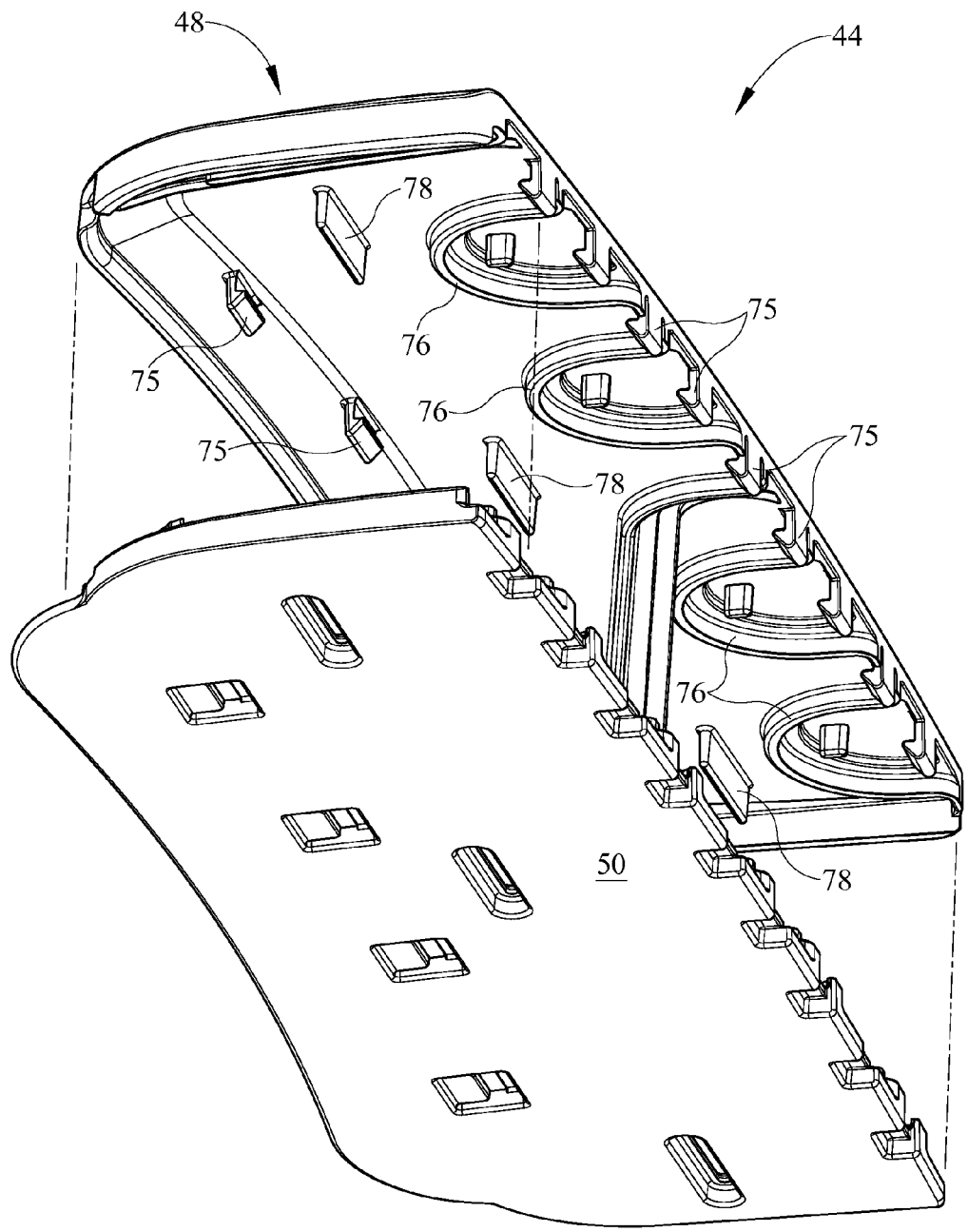
FIG. 7 depicts a lower perspective view of an exploded anchor and the upper surface of a cover portion of the anchor.

Referring now to FIG. 7, a lower perspective view of the anchor 44 is depicted in perspective view. The lower surface of cover 48 is shown having a plurality of cleat guides 76 which correspond to cleats 56 in order to provide a guide for the cord 51 (not shown). The cover includes a plurality of latches 75 depending downwardly which engage portions of the base 50 to retain the anchor 44 together. Additionally, the cover 48 may include a plurality of pillars 78 to strengthen the interconnection between the cover 48 and base 50.

Figure 8:
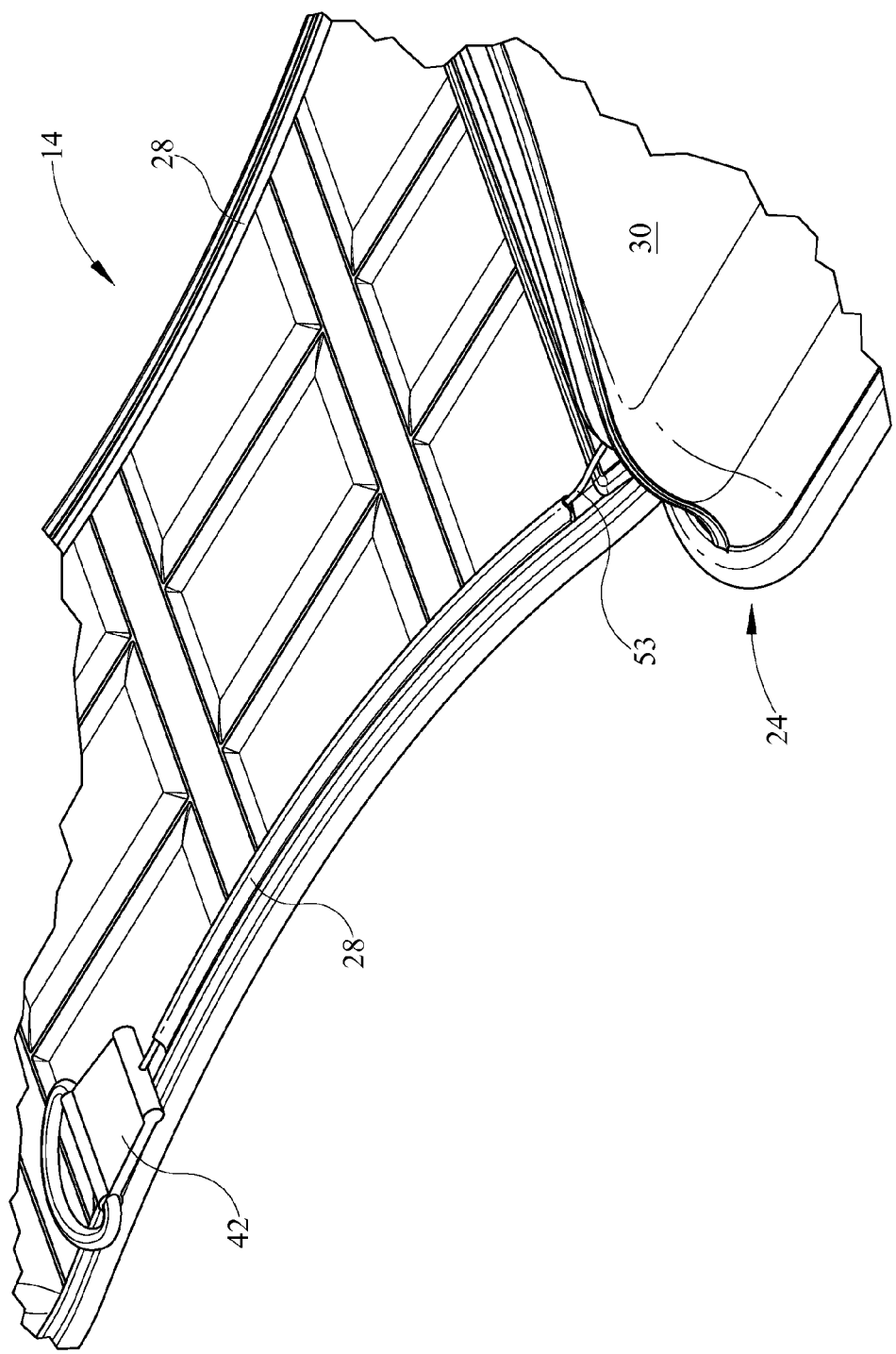
FIG. 8 depicts a detail perspective view of the cord routing through a housing.

Referring now to FIG. 8, the detailed perspective of the cable housing 28 is shown with the lower cable 53 passing through the central portion, through the cable housing 28 and connected to the lower pull 42. The cable housing 28 may be formed of nylon, polyester or other known wear resistant material which is capable of attachment to the panel portions 14, 16.

Figure 15:
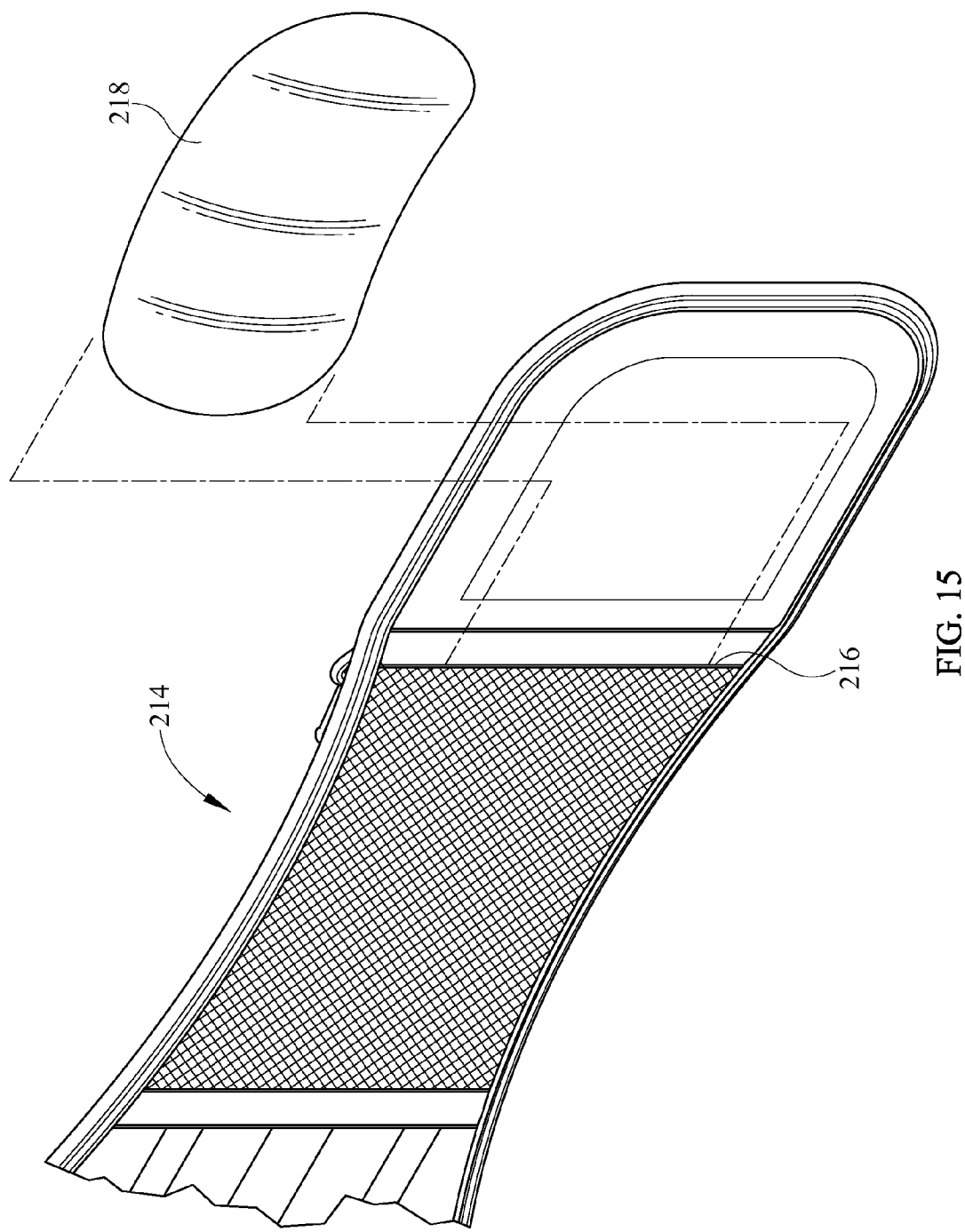
FIG. 15 depicts a perspective view of an alternative panel portion having a lateral or side pad.
Figure 16:
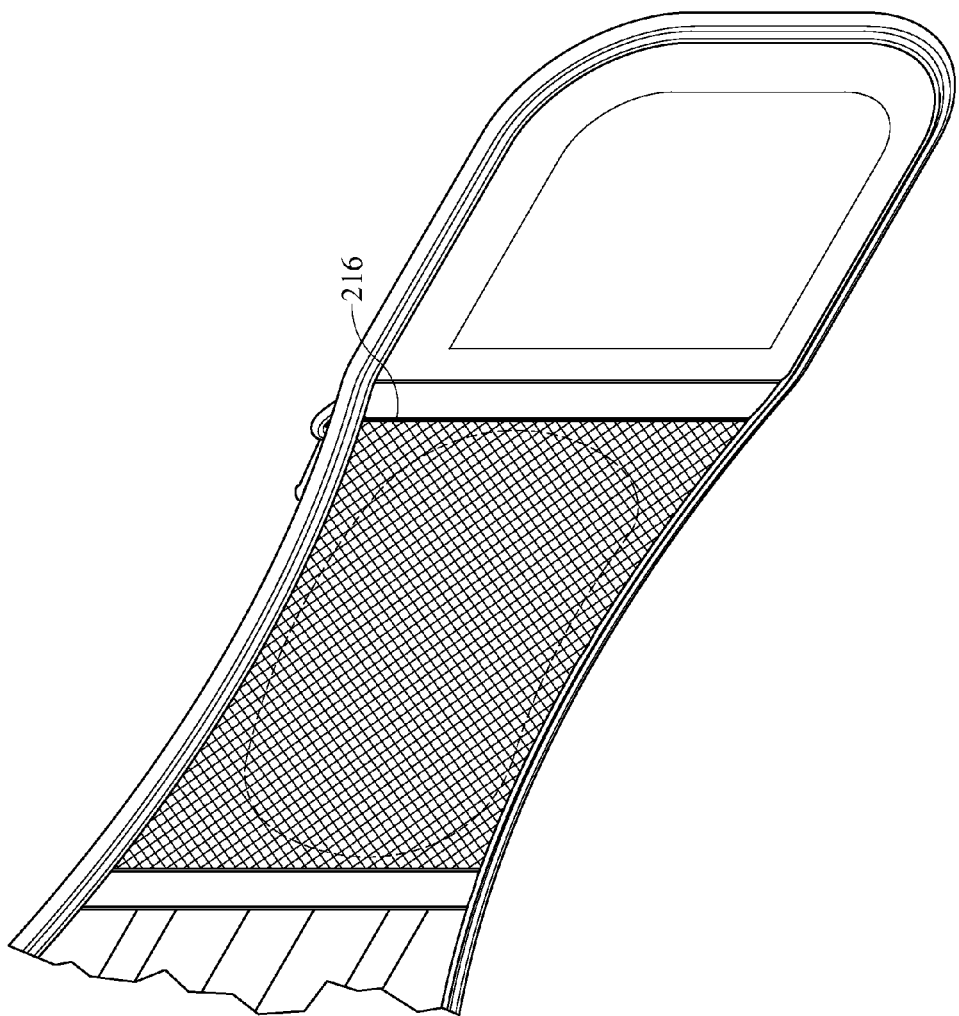
FIG. 16 depicts a perspective view of a panel portion with the lateral pad of FIG. 15 therein; and, FIG. 17 depicts an alternative cord system utilizing a strap extending from the anchors.

Also shown in the FIG. 8 are a plurality of ribs 22 along the panel portion 14. These ribs, as previously mentioned, may provide stiffening or may alternatively aid in gripping the user's body or clothing when utilized. As an alternative, the rib material may be replaced or additionally utilized with stiffened lateral pads 218, as shown in FIGS. 15 and 16.

Figure 9:
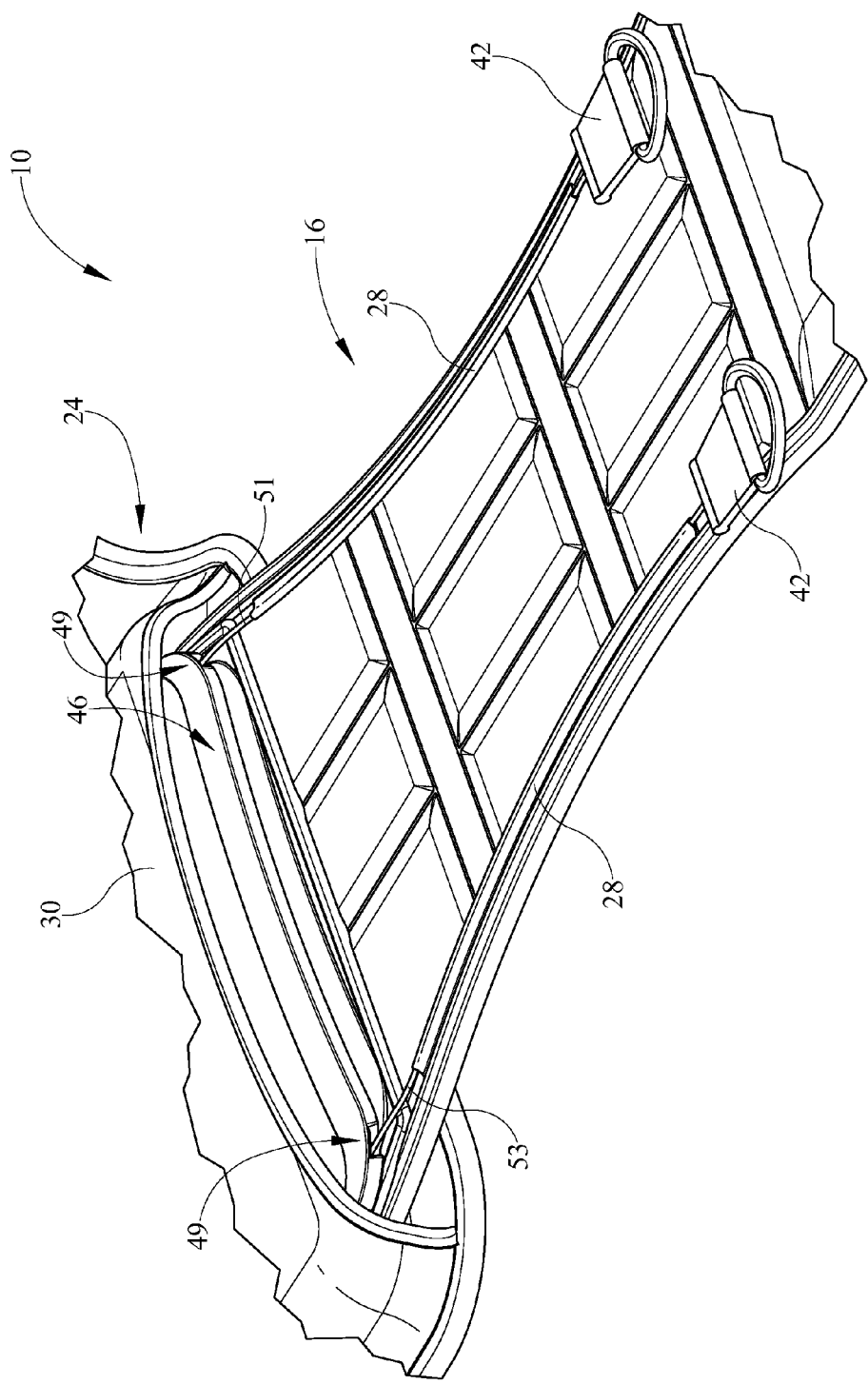
FIG. 9 depicts a perspective view of a second panel portions.

Referring to FIG. 9, the cord paths of the upper and lower cords 51, 53 are shown exiting the anchor 46 along the upper and lower edges of the second panel portion 16 through cord housing 28 to upper and lower pulls 42. The figure also depicts pathways 49 into the anchor 46 for the cords 51, 53. Additionally, as shown in this Figure, the pulls 42 are resting on the panel portion. However, the panel portion is shown flat, in a horizontal plane, whereas in use the panel portion would be oriented in a vertical plane. In order to provide a method of retaining the pulls 42 in position, rather than dangling loosely, the pulls 42 may also comprise a hook and loop fastening or closure material on at least one side. This hook and loop material may cooperate with hook and loop material on the panel portion to form a retaining mechanism for the pulls 42.

Figure 10:
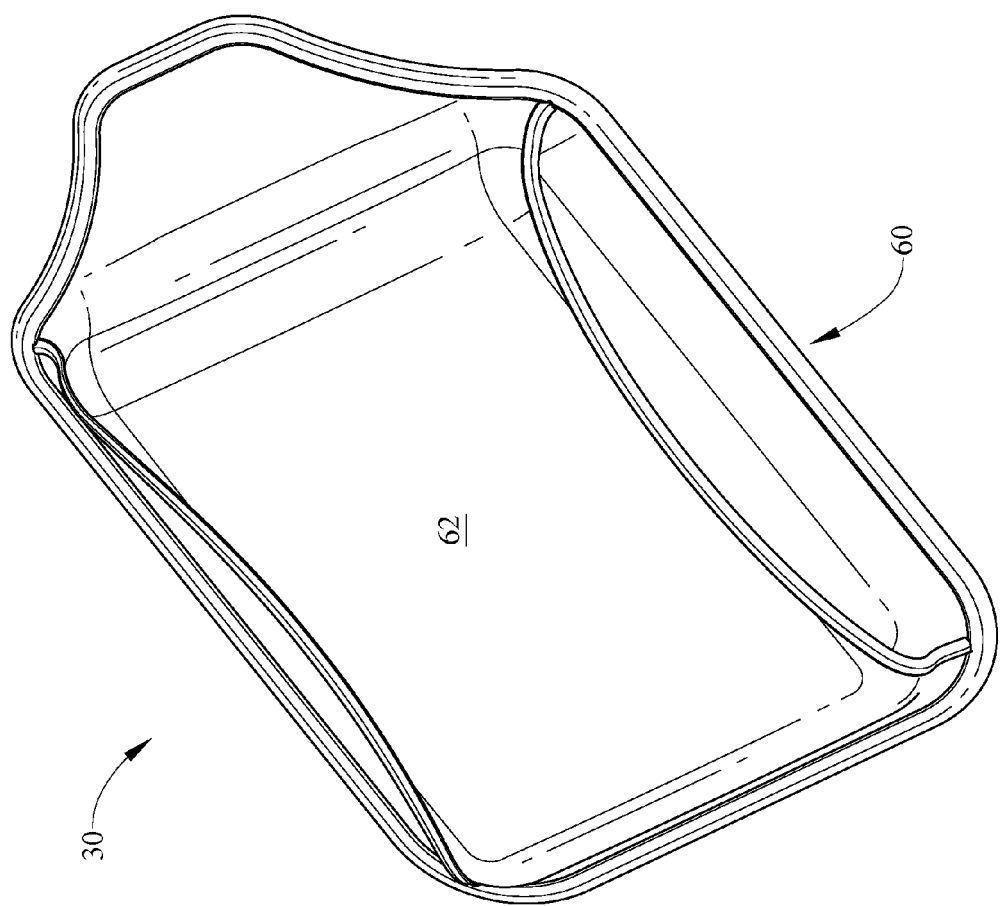
FIG. 10 depicts a perspective view of the sleeve.

Referring now to FIG. 10, the sleeve 30 is depicted in perspective view. The sleeve 30 includes an inner portion 60 which is disposed against the user's back or clothing and an outer portion 62 which passes along the anchor 44, 46 side of the brace 10. The sleeve 30 defines a pathway between portions 60 and 62 wherein the first and second panel portions 14, 16 may pass so that the sleeve 30 is positioned over the central portion 24. The sleeve 30 provides a cover for the moving anchors 44, 46. The sleeve 30 also provides an aesthetically pleasing appearance for the brace 10. Additionally, as previously discussed, a reinforcing element may be disposed within the sleeve 30 to provide additional support for a user.

Figure 11:
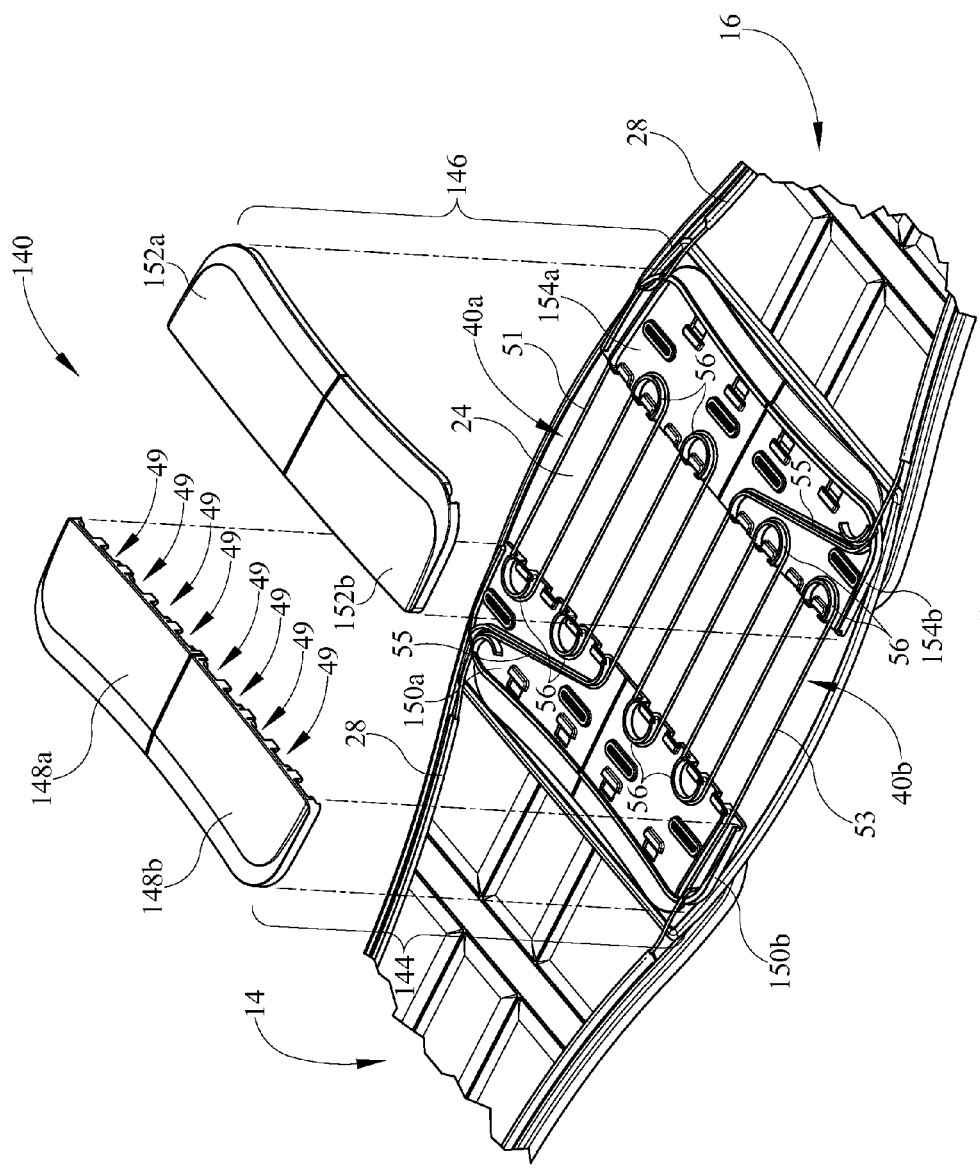
FIG. 11 depicts an alternative anchor design.

Referring now to FIG. 11, an alternative cord system 140 is depicted in perspective view. The cord system 140 utilizes anchors 144, 146 which have independent upper and lower portions. This allows for more specific adjustment of left side, right side, upper and lower sections of the anchors 144,146. Specifically, the anchor 144 has an upper cover 148a and upper base 150a. Anchor 144 also comprises a lower cover 148b and a lower base 150b. Similarly, the anchor 146 comprises an upper cover 152a and an upper base 154a as well, the anchor 146 comprises a lower cover 152b and a lower base 154b. This design is achieved by cutting the anchors 144, 146 along a line between ends 18, 20 of the panel portions 14,16. This design may provide additional independent adjustment of the upper and lower ends of the anchors 144, 146, as opposed to the single-anchor-per-side of the previous embodiment.

Figure 12:
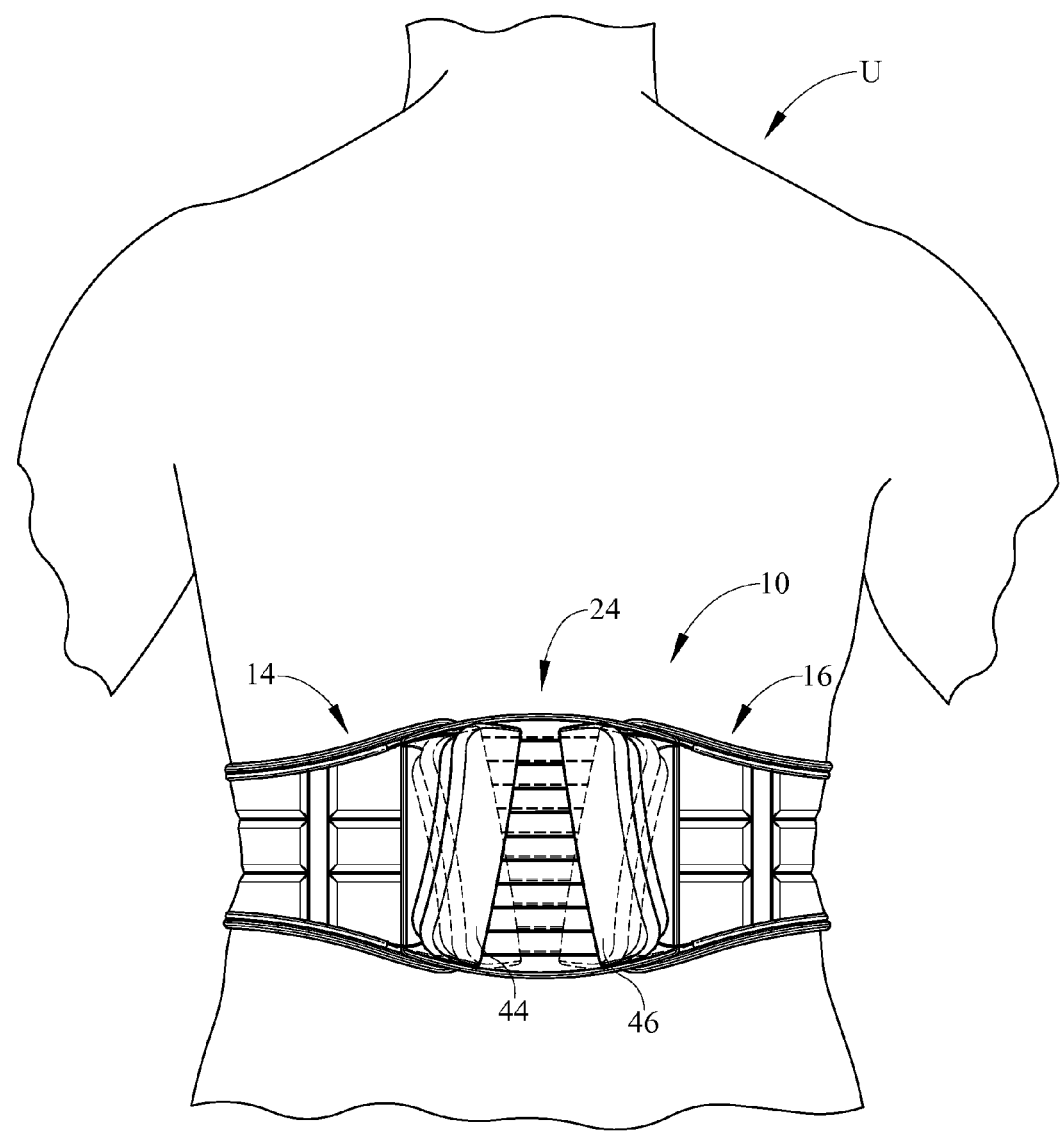
FIG. 12 depicts a rear view of a user wearing the orthotic brace with the anchors adjusted in various positions.

Referring now to FIG. 12, a rear view of the brace 10 is depicted wherein the central portion 24 is disposed in the lower central area of the user's (U) back. The anchors 44,46 are shown but the alternative anchors 144,146 may alternatively be utilized. The anchors 44,46 are depicted such that the upper ends are closer together than the lower ends. This configuration, shown in solid lines, is achieved by pulling the upper pulls 42. Alternatively, the lower pulls 42 may be pulled to angle the lower ends of the anchors closer together, as shown in broken line. As a further alternative, all pulls 42 may be pulled to tighten both upper and lower ends of the anchors 44, 46 providing a tighter fit and improved adjustability of the brace 10.

In use, the brace 10 is wrapped about the user's torso and the ends 18, 20 are connected, in the front of the torso, by means of closures 19, 21. The central portion 24 must be positioned in the lower back area of the user or ensured that it is properly positioned before tightening of the brace 10. Next, at least one of the lower and upper cord systems 40a, 40b are tightened, for example the lower cord and pulls 42 are tightened to cause spinal lift, relieving pressure on the spine and nerves in the lower spine region. Afterward, the upper cord and pulls 42 are tightened to at least retain and possibly enhance the lift provided from the lower cord and cord system 40b. The ends of either cord 51, 53 may also be pulled independently in order to tighten a single side, thus allowing for independent adjustment of the upper and lower portions as well as left and right portions of the central portion 24 of the brace 10. This same procedure may be utilized with the embodiment of FIG. 11. In either event, the orthotic brace 10 enhances conformity with the user's body and provides an improved anatomically correct, ergonomic fit.

Figure 13:
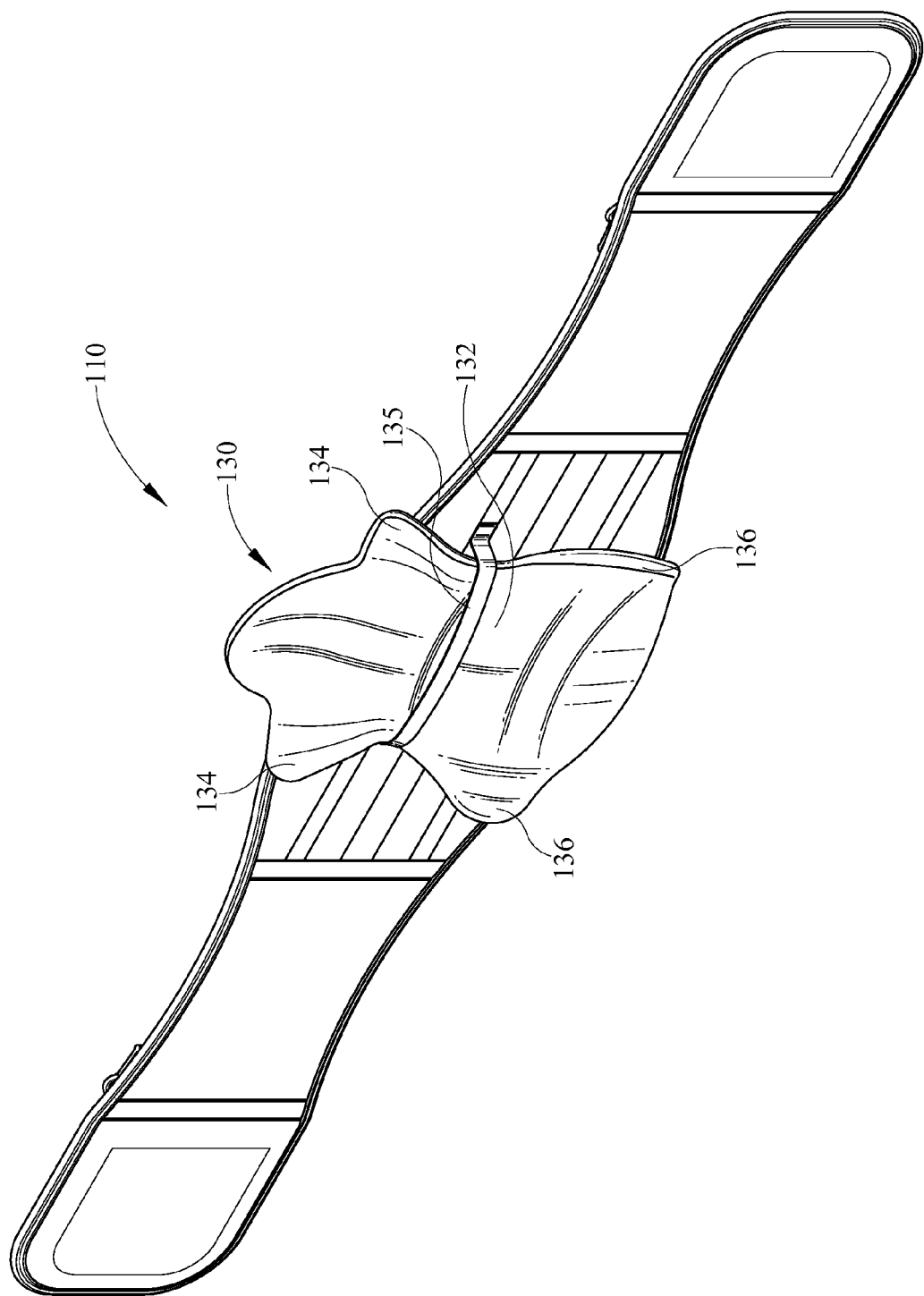
FIG. 13 depicts a perspective view of the orthotic brace with an alternative pad.

Referring now to FIG. 13, a perspective view of an alternative orthotic brace 110 is depicted. The brace 110 differs from the brace 10 by use of a sleeve 130 including an anatomically correct reinforcing element 132 which approximates the lordotic curvature of the lower back of a user. As previously discussed, the sleeve 130 and pad 132 may slide on and off of ends of the belt 110. As an alternative, as shown, the pad or reinforcing element may be held in position beneath an elastic strap 135. The strap may extend laterally between the first and second panel portions or may terminate on the central portion of the panel. In either event, the strap 135 is stretched so that the pad 132 may be positioned through strap 135 and against the brace 110. When released, the strap tightens against the pad 132 to retain it in position. When the pulls 42 are used to tighten the belt 110, the pad 132 conforms to the shape of the user's lower back, in turn providing increased lift and stabilization of the spine.

Figure 14:
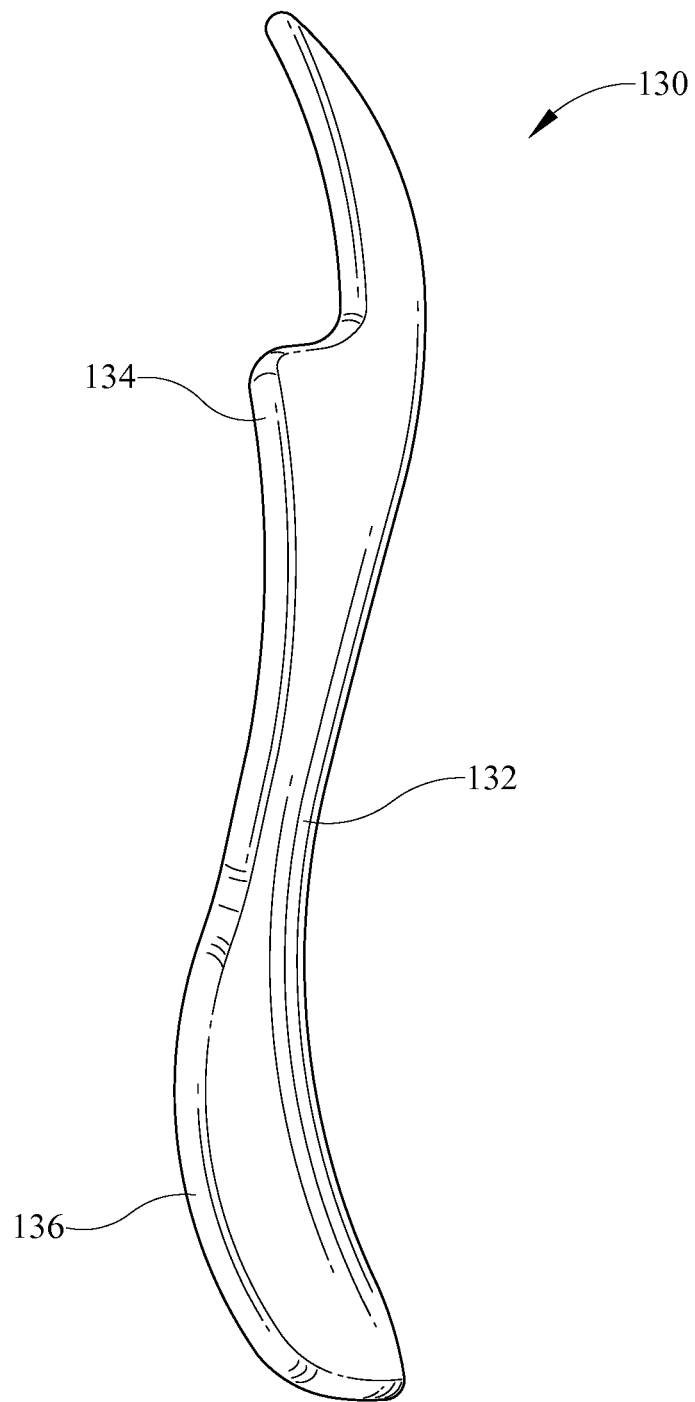
FIG. 14 depicts a side view of the alternative back pad of FIG. 13.

As shown in FIG. 14, the pad 130 is curved generally about two horizontal axes, providing a close approximation of the lordotic curvature of the user's lower back shape or curvature. Additionally, and referring also to FIG. 13, the pad 132 may include a first pair of upper wings 134 which enhance engagement with the wearer. Further, the pad 132 may also include a pair of lower wings 136 which also engage sides of the user and enhance engagement and support. The pad 132 may be formed of a thermoplastic or other lightweight metal or plastic-like material. Additionally, the pad 132 may be covered in a material to make the structure more aesthetically pleasing. For example, the material may be a moisture wicking material to improve performance and comfort of the product.

Referring now to FIG. 15, an alternative first side portion 214 is depicted in perspective view. The alternative first side portion is shown having a pocket 216 wherein a pad 218 is disposed. The pad 218 is oblong in shape and generally curved about both vertical and horizontal axes. The curvature allows the pad 218 to fit snugly in the waste area of the user. As shown in the exemplary embodiment, the pocket 216 is formed of a mesh material allowing for easy insertion or removal of the pad 218. According to the instant embodiment, the pad 218 may be formed of a plastic or other such elastomeric which may provide added support to the wearer as the pulls 42 are tightened. As shown in FIG. 16, the pad 218 is inserted into the pocket 216. Further, although the pad 218 is shown in only one of the sides of the brace 10, if the pad 218 is utilized, it is to be understood that one pad would be used on each side of the central portion of the brace.

When the upper and lower pulls 42 are used to move the anchors 44, 46, the lower pulls force the reinforcing element or pad 132 into the lordatic curve causing spinal lift. Next, the upper pulls are used to force the upper portion of the pad 132 into the user and, in a sense, lock the pad 132 against the spine. This causes lift and aids back muscles to hold the spine in a more anatomically correct position which further protects lumbosacral structures.

Figure 17:
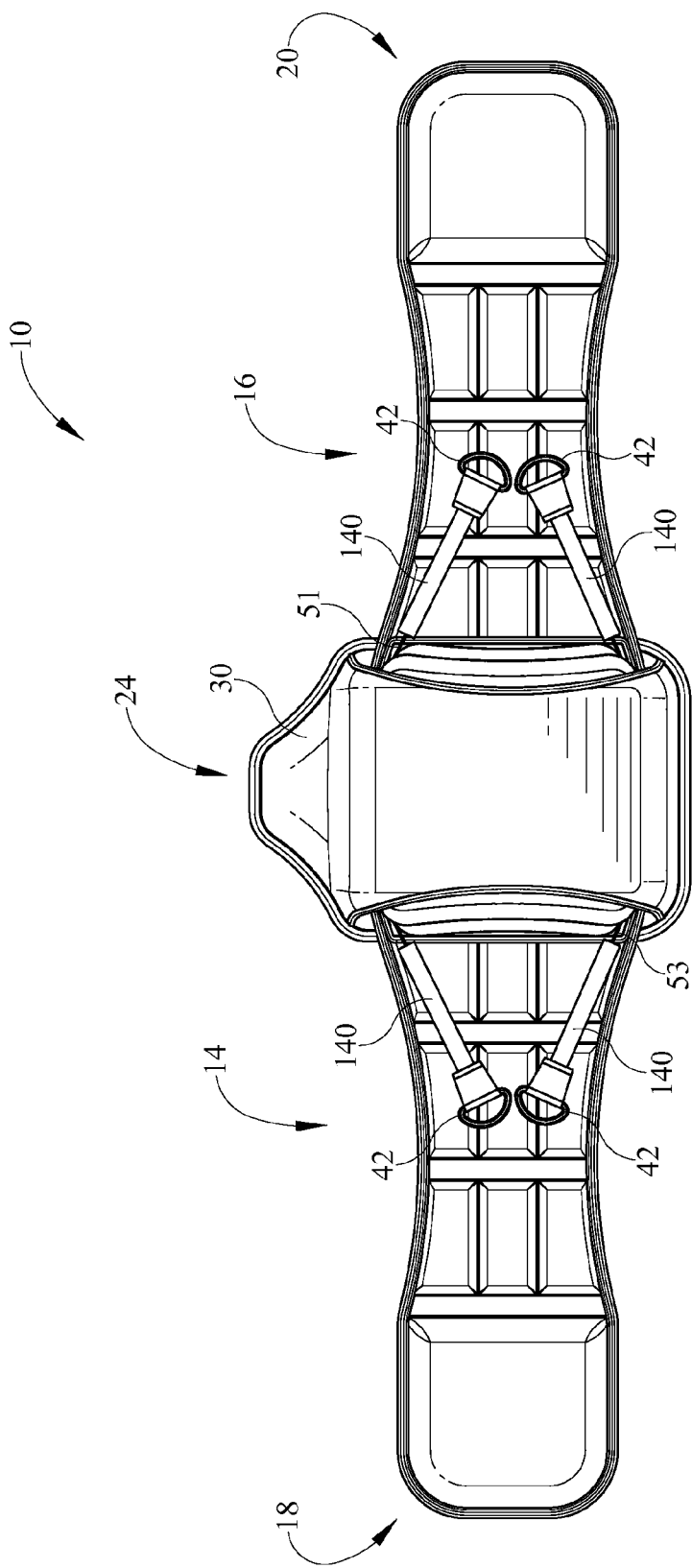

Referring now to FIG. 17, a rear view of the brace is shown having an alternative embodiment. The brace 10 is depicted with the various components previously described. However, according to a further alternative, the cord systems 40a, 40b utilize straps 140 which are connected to the cords 51, 53. The straps 140 may be formed of nylon or other known materials and extend from the pulls 42 toward the central portion 24. The straps 140 provide some stiffening to the cords 51, 53 and may eliminate the need for the housings, through which the cords pass in the previous embodiment. According to such embodiment, the cords 51, 53 may exit the anchors 44, 46 and then are covered by the straps 140.

The foregoing description of several embodiments of the invention has been presented for purposes of illustration. It is not intended to be exhaustive or to limit the invention to the precise steps and/or forms disclosed, and obviously many modifications and variations are possible in light of the above teaching. It is intended that the scope of the invention and all equivalents be defined by the claims appended hereto.

The invention claimed is:

1. An orthotic brace, comprising:
   a panel having a central portion, a first side panel portion and a second side panel portion, said panel being of sufficient length to wrap around a user's torso;
   a cord system including opposed cord anchors disposed generally centrally on said panel;
   a first cord connected to said anchors for adjustment of a lower portion of said system and a second cord connected to said anchors for adjustment of an upper portion of said system;
   said first cord having a first upper pull and a second upper pull;
   said second cord having a first lower pull and a second lower pull;
   said cord system allowing for separate tensioning of first side, second side, upper and lower portions of said cord system to provide improved conformance to said user's torso;
   a sleeve removably disposed about said central portion of said brace.

2. The orthotic brace of claim 1, wherein said anchors comprising a base and a cover.

3. The orthotic brace of claim 2, wherein said anchors further comprising cleats disposed between said base and cover, said cleats increasing mechanical advantage of said cord system.

4. The orthotic brace of claim 1, wherein said anchors are movable within said sleeve.

5. The orthotic brace of claim 1 further comprising pockets disposed in said first and second panel portions and a pad disposed in each of said pockets.

6. An orthotic brace, comprising:
   a panel having a first portion and a second portion, said first portion and said second portion extending from a central portion;
   a closure mechanism disposed at at least one end of said first portion or said second portion;
   a cord system having movable first and second anchors disposed on said central portion of said panel, said cord system having an upper cord system and a lower cord system for upper and lower adjustment of each of said first and second anchors;
   a pad disposed on said central portion on a side of said central portion opposite said first and second anchors.

7. The orthotic brace of claim 6, wherein said pad being generally flat.

8. The orthotic brace of claim 6, wherein said pad having a lordotic curvature contoured to approximate the curvature of a user's lower back.

9. The orthotic brace of claim 8, wherein said pad further comprising wings disposed at upper and lower ends of said pad.

10. The orthotic brace of claim 6, wherein said cord system providing a mechanical advantage of between about 4:1 and about 8:1.

11. A method of using an orthotic brace, comprising:
    wrapping said brace having a central panel portion and opposed side panel portions about a user's torso;
    closing said brace with a closure mechanism;
    ensuring said central portion is properly positioned at a lower back of said user;
    pulling a first cord system capable of independently tightening upper portions of left and right upper anchors connected to said central panel portion;
    pulling a second cord system capable of independently tightening lower portions of said left and right anchors of said central panel portion.

12. The method of using an orthotic brace of claim 11, pulling said lower cord system firstly to move anchors connected to said central panel portion.

13. The method of claim 12, pulling said lower cord system secondly to move anchors connected to said central panel portion.

14. The method of claim 11 further comprising pulling first and second pulls of said upper cord system and said lower cord system to tighten both left and right sides of said panel portion.

15. An orthotic brace, comprising:
    a flexible panel having a first panel portion, a second panel portion and a central portion connecting said first and second panel portions, said first panel portion and said second panel portion being of sufficient length to wrap around a torso of a user;

a closure structure disposed near ends of said first and second panel portions to secure said flexible panel about said torso;

an upper cord system and a lower cord system connected to said panel, said upper and lower cord systems being independently adjustable for a more anatomically correct fit and providing a mechanical advantage;

said upper cord system and said lower cord system each having a first pull and a second pull, movable along upper and lower edges of said first and second panel portions, respectively;

said first pull disposed at one of said first panel portion and said second panel portion, said second pull disposed at the other of said first panel portion and said second panel portion;

wherein right side and left sides of said upper and lower cord systems may be tightened independently to tighten or loosen upper and lower portions of said orthotic brace at said central portion; and, a slidable sleeve.

16. The orthotic brace of claim 15 wherein said sleeve is disposed over a central portion of said orthotic brace.

17. An orthotic brace, comprising:

a flexible panel having a first panel portion, a second panel portion and a central portion connecting said first and second panel portions, said first panel portion and said second panel portion being of sufficient length to wrap around a torso of a user;

a closure structure disposed near ends of said first and second panel portions to secure said flexible panel about said torso;

an upper cord system and a lower cord system connected to said panel, said upper and lower cord systems being independently adjustable for a more anatomically correct fit and providing a mechanical advantage;

said upper cord system and said lower cord system each having a first pull and a second pull, movable along upper and lower edges of said first and second panel portions, respectively;

said first pull disposed at one of said first panel portion and said second panel portion, said second pull disposed at the other of said first panel portion and said second panel portion;

wherein right side and left sides of said upper and lower cord systems may be tightened independently to tighten or loosen upper and lower portions of said orthotic brace at said central portion;

said upper and lower cord systems further comprising cord anchors which are movably connected to said flexible panel;

said cord anchors being movable within a sleeve.

* * * * *